July 13, 1954 O. OBERTELLO Plant Pat. 1,289
ROSE PLANT
Filed March 30, 1953
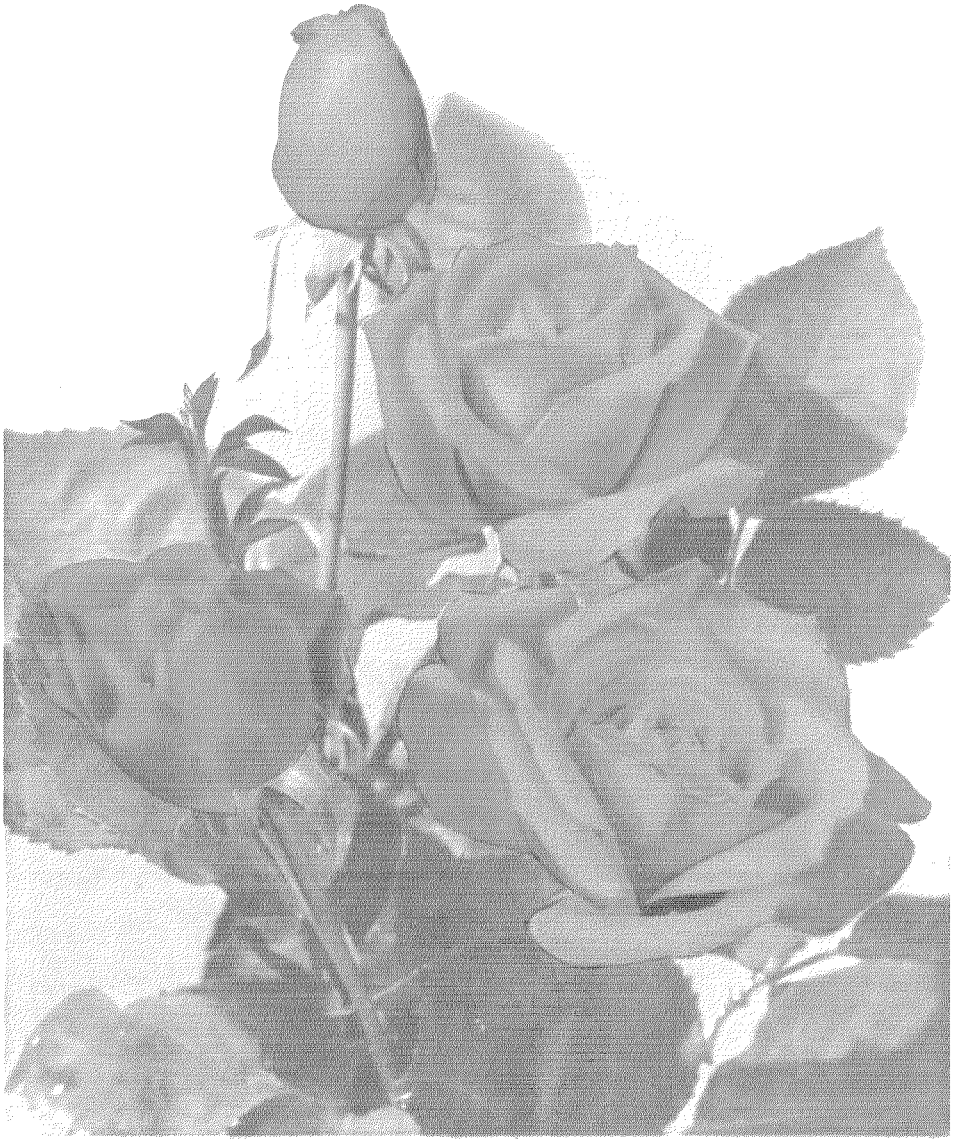
INVENTOR
Orlando Obertello
By Orville M. Kile
Plant pat. Agent Patented July 13, 1954

Plant Pat. 1,289

UNITED STATES PATENT OFFICE 1,289

ROSE PLANT

Orlando Obertello, Oakland, Calif.

Application March 30, 1953, Serial No. 345,749

1 Claim. (Cl. 47—61)

My present discovery pertains to a new and distinct variety of rose plant in the red-flowered, hybrid-tea class. Its distinction lies principally in its combination of good qualities, with particular emphasis on its healthy growth and the difference in color and petalage of its flowers as compared with similar varieties.

The new variety originated at my greenhouses near San Francisco, California, as a cultivated sport of the variety Vierlanden (unpatented). Asexual reproduction of the variety by budding at the same location has shown the same qualities as found in the original sport to be well fixed.

Accompanying illustrations show four specimens of the flowers of my new variety in various stages of opening, together with some of the foliage and stems. These are in approximately true colors, as depicted by a color photograph.

In the following detailed description, color plate references indicate Ridgway's Color Standards and Nomenclature. Other color references indicate the ordinary dictionary meaning of the term.

*The plant*

Growth habit: Erect compact bush. Vigorous, with average height of about 2½ feet. Breaks freely, producing many heavy canes.

Canes: Heavy and sturdy.

Hardiness: Average.

Blooming habit: Continuous and free bloomer, producing about 20% more cut flowers than similar varieties now on the market.

Stems: Slender but strong. Approximately Cedar Green (Pl. VI). Thorns sharp, slender, downward-pointing, slightly hooked, light greenish-tinged, position irregular.

Disease resistance: When grown under similar circumstances or nearby, my new variety has shown much less mildew than Red Delight and Victory Red—the two varieties most like it.

Foliage:

*Type.*—Pinnately compound, 3 to 5 leaflets.

*Quantity.*—Abundant.

*Size.*—Large, terminal leaflet approximately 3 inches long by 2 inches wide. Pair of lateral leaflets next stem very much smaller, approximately 1½ inches long by 1 inch wide.

*Shape.*—Oval, with acuminate apex which is very frequently turned to one side.

*Color.*—Dark green, approximately Varley's Green (Pl. XVIII). New foliage approximately Vinaceous-Rufous to Hay's Russet (Pl. XIV).

*Serrations.*—Sharp; pronounced; single.

*Texture.*—Moderately soft and leathery. Smooth.

*Rachis.*—Slender; grooved on upper side; smooth below.

*Stipules.*—Narrow; clinging.

*Bloom*

Bud:

*Size.*—Large, approximately 1¾ inches long when ready to unfold.

*Form.*—Ovoid.

*Opening.*—Slow and even.

*Color.*—Between Scarlet and Nopal Red (Pl. I).

*Peduncle.*—Slender; strong; relatively short (about 3½ inches long); slightly lighter green than stems.

Flower:

*Borne.*—Singly.

*Size.*—Large, up to 5 inches in diameter when fully open.

*Form.*—Cone-shaped center, with outer petals extending above it. Develops into a large bloom with petals reflexing only very slightly at edge. Petals remain upright for some time but eventually spread to reveal stamens and petals in center.

*Petalage.*—Usually 35 to 45 petals.

*Color.*—Fall flowers are a uniform color popularly known as Cardinal Red, which lies between Scarlet and Nopal Red (Pl. I). Winter color is somewhat darker. Has small aiglet of light yellow, approximately Baryta Yellow (Pl. IV).

*Fragrance.*—Abundant; spicy.

*Lasting quality.*—Flower lasts exceedingly well, particularly when cut.

Petals:

*Size.*—Outer petals large, approximately 2¼ to 2½ inches in each direction.

*Shape.*—Almost round, with edge slightly notched and waved. Deep-cupped.

*Texture.*—Substantial but not heavy.

*Appearance.*—Inside surface very velvety; outside silky.

Reproductive organs:

*Pistils.*—A great many (about 100); bunched; partly enclosed. *Styles.*—Exposed portion short and approximately Carmine (Pl. I). *Stigmas.*—Yellowish color, approximately Baryta Yellow (Pl. IV).

*Stamens.*—Many; set outside pithy ring encircling pistils; curved toward pistils. *Filaments.*—Curved; reddish-tinged. *Anthers.*—Large; bright yellow, approximately Light Cadmium (Pl. IV).

*Comparison*

The variety most like my own is Victory Red (Plant Patent No. 369), but differs principally as follows. My new variety:

1. Has a greater petalage than Victory Red.
2. Has a much brighter red flower, which is more fragrant.
3. Has larger and more abundant foliage.
4. Produces a more bushy plant and is not so tall.
5. Produces heavier canes.
6. Is a more prolific bloomer, producing approximately 20% more cut flowers.
7. Has blooms of a different form, not being so high-centered and not showing its stamens and pistils so quickly.
8. Is less susceptible to mildew.

The variety Red Delight (unpatented) is next in its similarity to my new variety. There are the same differences between it and my new variety as those given above in comparison with Victory Red, with the addition that my new variety is a much better grower, producing more and heavier canes, and is much less susceptible to mildew than Red Delight.

Having thus disclosed my discovery, I claim:

The new and distinct variety of hybrid tea rose plant, substantially as herein shown and described, characterized particularly by its combination of healthy, bushy plant growth; strong, heavy canes; abundance of large foliage which is soft and smooth but leathery; and large fragrant flowers of compact form, medium petalage, and bright red color.

No references cited.